United States Patent
Sparks

(10) Patent No.: US 7,524,454 B1
(45) Date of Patent: Apr. 28, 2009

(54) SANITATION METHOD FOR DISINFECTION OF ENCLOSED SPACES

(75) Inventor: David W. Sparks, Thonotosassa, FL (US)

(73) Assignee: Zimek Technologies IP, LLC, Tampa, FL (US)

( * ) Notice: Subject to any disclaimer, the term of this patent is extended or adjusted under 35 U.S.C. 154(b) by 437 days.

(21) Appl. No.: 11/200,653

(22) Filed: Aug. 10, 2005

Related U.S. Application Data

(60) Provisional application No. 60/600,252, filed on Aug. 10, 2004.

(51) Int. Cl.
*A61L 2/025* (2006.01)

(52) U.S. Cl. ............................ 422/20; 422/128; 422/28; 239/4; 239/102.2

(58) Field of Classification Search .................... 422/20, 422/28, 128; 239/4, 102.2
See application file for complete search history.

(56) References Cited

U.S. PATENT DOCUMENTS 3,957,252 A * 5/1976 Storz ........................... 366/118
5,176,856 A 1/1993 Takahashi et al.
5,300,260 A 4/1994 Keshet et al.
6,511,050 B2 1/2003 Chu
6,680,041 B1 1/2004 Kumar et al.
6,883,724 B2 4/2005 Adiga et al.

FOREIGN PATENT DOCUMENTS

JP          54082708 A    *    7/1979
JP          07-213968          *    8/1995

OTHER PUBLICATIONS

English abstract for JP 07-213968.*
English abstract for JP 54082708 A.*

* cited by examiner

*Primary Examiner*—Sean E Conley
(74) *Attorney, Agent, or Firm*—Allen, Dyer, Doppelt, Milbrath & Gilchrist, P.A.

(57) ABSTRACT

A device for sanitizing a space includes a tank for holding an aqueous sanitizing liquid. A pair of ultrasonic heads is provided, wherein each head has a plurality of vibratable discs for generating ultrasonic energy. A device for vibrating the discs is provided to form an atomized fog of particles from the liquid. A pair of flotation supports float atop the liquid in the tank, each having means for holding a head atop the liquid. A fan is positioned above the supports for distributing the fog throughout a space. The device may also be used to distribute a liquid by creating the atomized fog as above and directing the fog to a desired location.

10 Claims, 4 Drawing Sheets

SANITATION METHOD FOR DISINFECTION OF ENCLOSED SPACES

CROSS-REFERENCE TO RELATED APPLICATION

Figure 1:
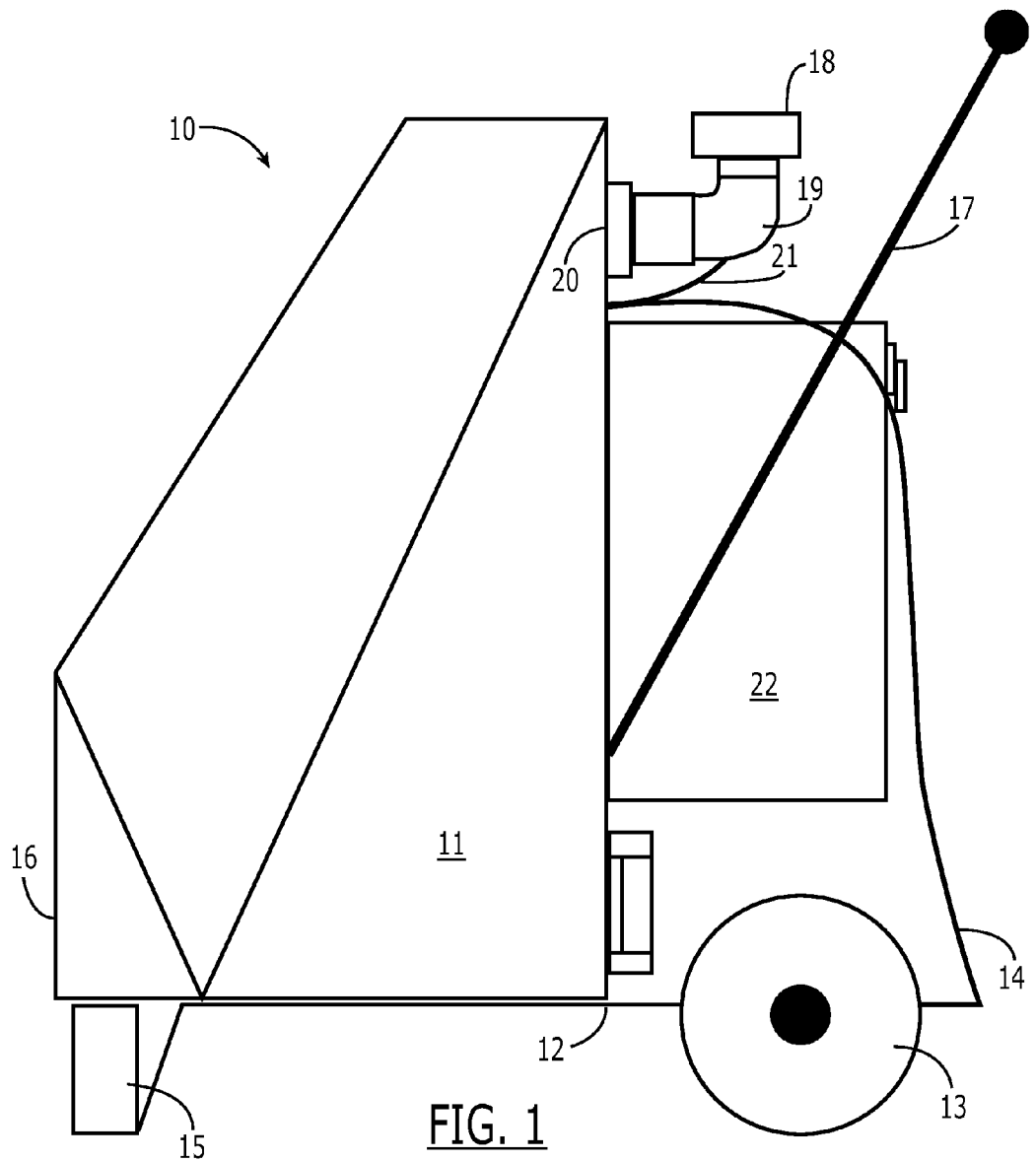
Figure 2:
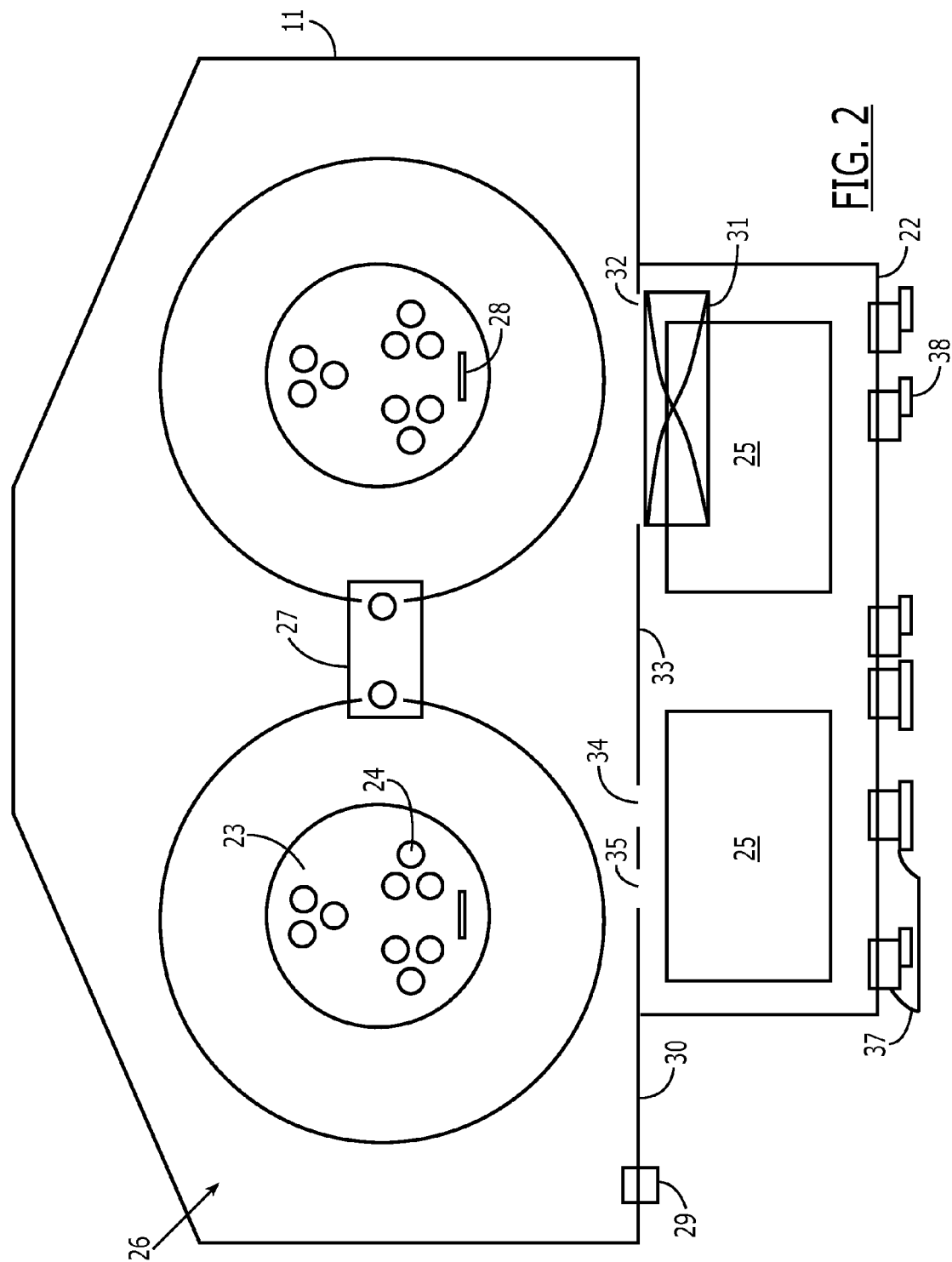
Figure 3:
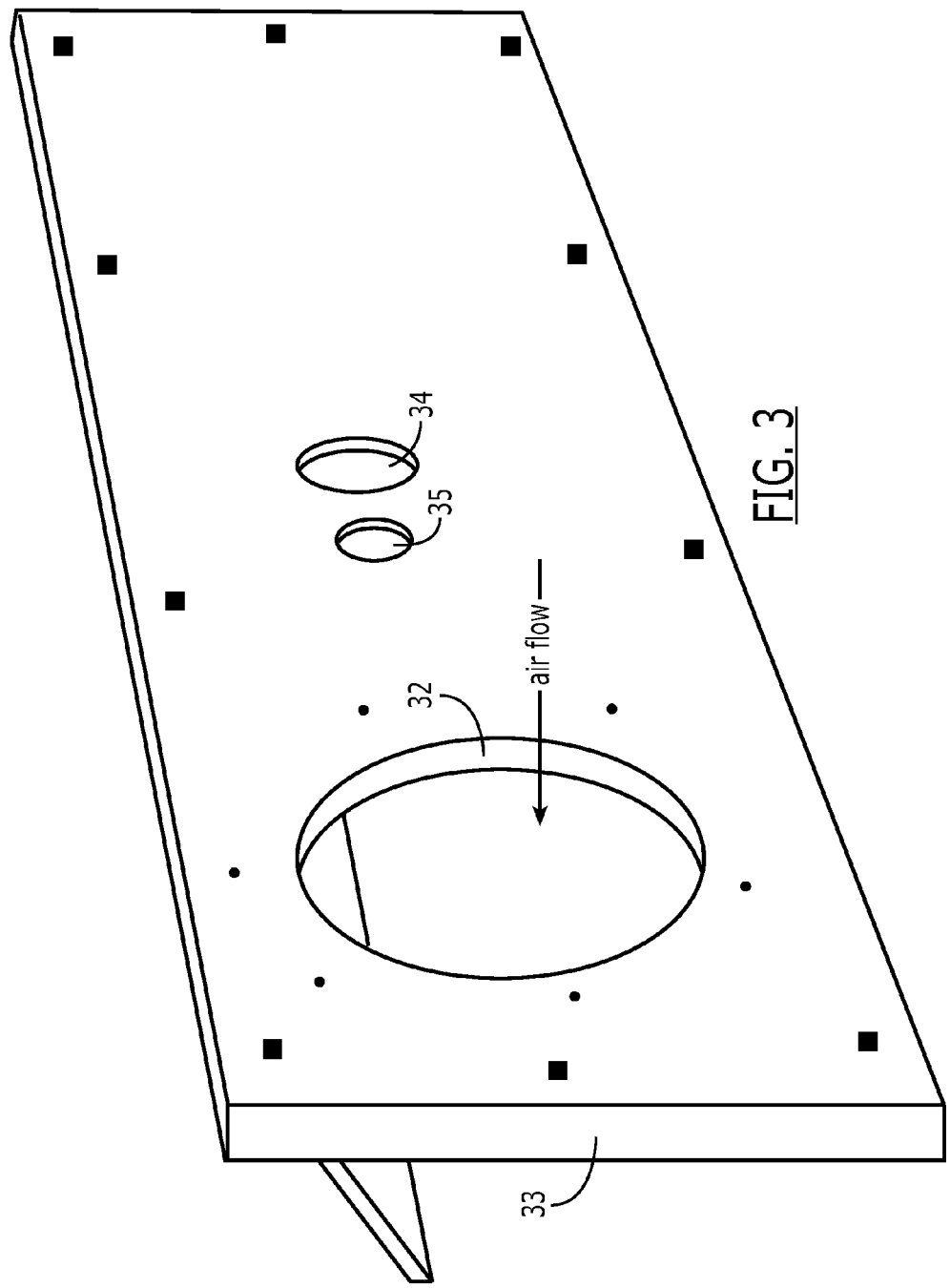
Figure 4:
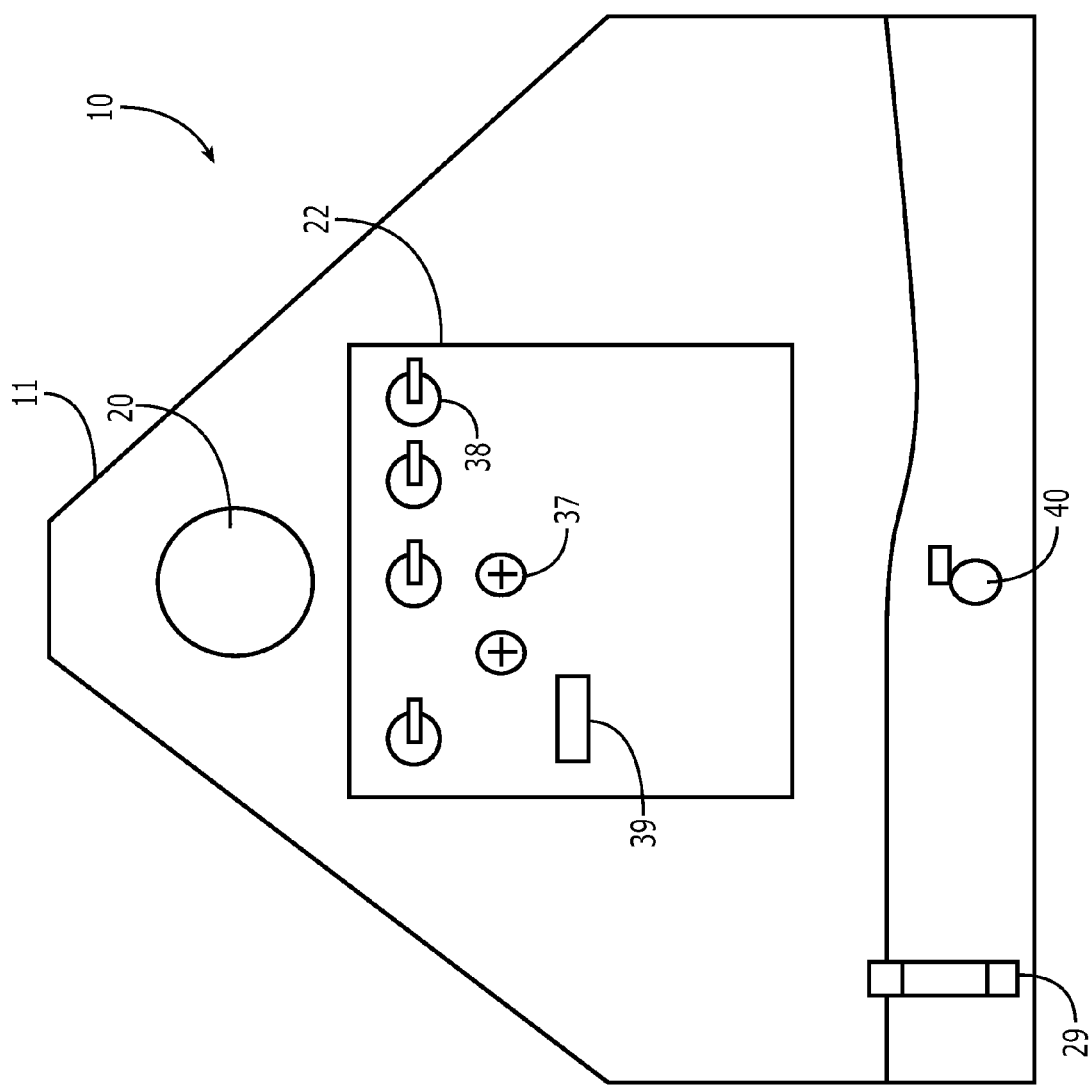

This application claims priority to provisional application Ser. No. 60/600,252, filed on Aug. 10, 2004, entitled "Sanitation System and Associated Methods for Disinfection of Enclosed Spaces."

BACKGROUND OF THE INVENTION

1. Field of the Invention

The present invention relates to systems and methods for sanitizing enclosed spaces, and, more particularly, to such systems and methods that are capable of treating spaces three-dimensionally.

2. Description of Related Art

The sanitization and disinfection of enclosed spaces has become an issue of increasing importance owing to the possible presence of both natural and deliberately introduced contaminants. Since most commercial buildings are "sealed," that is, their windows cannot be opened, circulation of "fresh" air is typically not possible within a particular room. Similarly, most houses are now effectively sealed, with mostly processed air being circulated. In addition, some forms of conveyance, especially airplanes, are of necessity sealed against the environment during flight.

The enclosed nature of modern spaces has led to such problems as "sick building syndrome," since molds and mildews can flourish in enclosed, damp environments, and also to the possibility of the deliberate introduction of more insidious threats to life, such as biological and chemical agents.

At present most sanitizing and disinfecting agents are "two-dimensional," that is, they are applied to accessible surfaces. For example, when cleaning a table, typically the cleanser is applied to the table top, but not the underside.

"Fogging" agents are known for eradicating pests such as fleas and other insects. Ionization-type purifiers are also known in the art that use electrostatic means to collect allergens and pollutants.

SUMMARY OF THE INVENTION

The present invention provides a device for sanitizing a space. The device comprises a tank for holding an aqueous sanitizing liquid. A pair of ultrasonic heads is provided, wherein each head comprises a plurality of vibratable discs for generating ultrasonic energy. A means for vibrating the discs is provided to form an atomized fog of particles from the liquid. A pair of flotation supports float atop the liquid in the tank, each having means for holding a head atop the liquid. A fan is positioned above the supports for distributing the fog throughout a space.

The device may also be used to distribute a liquid by creating the atomized fog as above and directing the fog to a desired location, for example, for delivering fertilizer or pesticide to a plot of land, for watering plants, or for distributing a skin-care product to the skin of a user, although these uses are not intended to be limiting.

The device of the present invention is able to reach all areas in a space where air can penetrate, and, since the atomized particles have been found to remain airborne longer than conventional mists, treatment is more thorough, and less chemical is required than used by previously known devices. A typical room can be disinfected in 10 min, for example.

The features that characterize the invention, both as to organization and method of operation, together with further objects and advantages thereof, will be better understood from the following description used in conjunction with the accompanying drawing. It is to be expressly understood that the drawing is for the purpose of illustration and description and is not intended as a definition of the limits of the invention. These and other objects attained, and advantages offered, by the present invention will become more fully apparent as the description that now follows is read in conjunction with the accompanying drawing.

BRIEF DESCRIPTION OF THE DRAWINGS

FIG. 1 is a side plan view of an embodiment of the sanitizing device of the present invention.

FIG. 2 is a top plan view of a horizontal cross-section of the interior of the device of FIG. 1.

FIG. 3 is a side-rear perspective view of the panel mount.

FIG. 4 is a rear plan view of the device.

DETAILED DESCRIPTION OF THE PREFERRED EMBODIMENTS

A description of the preferred embodiments of the present invention will now be presented with reference to FIGS. 1-4.

A device 10 for distributing an atomized fog of liquid is included in the present invention (FIG. 1). The device 10 comprises a tank 11 for holding a liquid, such as, but not intended to be limited to, a sanitizing liquid. Typically the tank 11 is mounted on a base 12 having a pair of wheels 13 rotatably affixed thereto along a rear edge 14 and a bottom support 15 along a front edge 16 for supporting the device 10 when not being wheeled about. A handle 17 extends from the rear of the tank 11. The device 10 also has an outlet 18 comprising an elbow joint 19 pointing upwards of the tank 11 and having an inlet 20 into the space above the liquid in the tank 11. A condensation drain 21 extends from the elbow joint 19 back into the tank 11. The control system for the device 10 is positioned within a housing 22 affixed behind the tank 11.

Within the tank 11 are positioned a pair of ultrasonic heads 23 (FIG. 2). Each head 23 comprises a plurality of vibratable discs 24 for generating ultrasonic energy in ways known in the art by means of a dc transformer 25 (e.g., two 120 to 36-V dc transformers) positioned within the housing 22. A pair of flotation supports 26 float atop the liquid in the tank 11. Each support 26 in a preferred embodiment comprises a toroidal element having a central hole adapted to hold a head 23 atop the liquid. The supports 26 are tethered together with a linkage 27 that is preferably inflexible. When the heads 23 are activated, the discs 24 are vibrated, and an atomized fog of particles of approximately 1-8 μm diameter is formed from the liquid. If the liquid level gets too low, a shutoff 28 on the heads 23 will deactivate the transformer 25. Additionally, the user can view the liquid level through a site glass 29 positioned through the rear wall 30 of the tank 11.

A fan 31 is positioned within a hole 32 in a panel mount 33 (FIG. 3) and above the supports 26 for distributing the created fog throughout a space. The panel mount 33 also includes an aperture 34 for leads between the heads 23 and the transformers 25 and an aperture 35 for passing the condensation drain 21 therethrough.

On the rear face 36 of the control system housing 22 (FIG. 4) are positioned control knobs 37 for setting timers and speed as desired, control switches 38, and a time meter 39. Along the bottom of the tank 11 is positioned a drain 40.

In the foregoing description, certain terms have been used for brevity, clarity, and understanding, but no unnecessary limitations are to be implied therefrom beyond the requirements of the prior art, because such words are used for description purposes herein and are intended to be broadly construed. Moreover, the embodiments of the apparatus illustrated and described herein are by way of example, and the scope of the invention is not limited to the exact details of construction.

What is claimed is:

1. A method for sanitizing a space comprising the steps of:
adding an aqueous sanitizing liquid to a tank;
supporting a pair of ultrasonic heads within the tank atop the liquid, each ultrasonic head supported with a separate flotation support, each head comprising a plurality of vibratable discs for generating ultrasonic energy;
tethering the flotation supports together;
vibrating the discs to form an atomized fog of particles from the liquid;
distributing the fog throughout a space, for disinfecting the space.

2. The method recited in claim 1, wherein the tank is held by a base.

3. The method recited in claim 1, further comprising controlling the vibrating and the distributing steps.

4. The method recited in claim 1, wherein each flotation support comprises a generally toroidal element having a central hole dimensioned to hold an ultrasonic head therein.

5. The method recited in claim 1, further comprising the steps of sensing a level of liquid in the tank and, responsive to the sensed liquid level, stopping the vibrating when a liquid level in the tank reaches a predetermined level.

6. The method recited in claim 1, wherein the vibrating step is performed with the use of a pair of transformers.

7. The method recited in claim 1, wherein the tethering step comprises tethering the ultrasonic heads together with an inflexible linkage.

8. The method recited in claim 1, wherein the atomized fog comprises particles having a diameter in a range of approximately 1-8 μm.

9. The method recited in claim 1, further comprising the step of viewing a level of liquid in the tank through a sight glass.

10. The method recited in claim 1, further comprising the steps of collecting condensate formed during the vibrating step and channeling the condensate back into the tank.

* * * * *